United States Patent
Walter et al.

(10) Patent No.: US 11,572,588 B2
(45) Date of Patent: Feb. 7, 2023

(54) METHODS OF EVALUATING TREATMENT EFFICACY AND/OR TREATMENT DURATION IN MYCOBACTERIAL DISEASES

(71) Applicants: The Regents of the University of Colorado, Denver, CO (US); The Regents of the University of California, Oakland, CA (US); Yale University, New Haven, CT (US); Colorado State University Research Foundation, Fort Collins, CO (US); The Board of Trustees of the Leland Stanford Junior University, Stanford, CA (US)

(72) Inventors: Nicholas D. Walter, Denver, CO (US); Martin Voskuil, Denver, CO (US); Gary Schoolnik, Denver, CO (US); Gregory Dolganov, Denver, CO (US); J. Lucian Davis, Fairfield, CT (US); Payam Nahid, Berkeley, CA (US); Greg Robertson, Fort Collins, CO (US); Anne Lenaerts, Fort Collins, CO (US)

(73) Assignees: The Regents of the University of Colorado, a body corporate, Denver, CO (US); The Regents of the University of California, Oakland, CA (US); Yale University, New Haven, CT (US); Colorado State University Research Foundation, Fort Collins, CO (US); The Board of Trustees of the Leland Standford Junior University, Stanford, CA (US)

( * ) Notice: Subject to any disclaimer, the term of this patent is extended or adjusted under 35 U.S.C. 154(b) by 0 days.

(21) Appl. No.: 16/632,310

(22) PCT Filed: Jul. 19, 2018

(86) PCT No.: PCT/US2018/042963
§ 371 (c)(1),
(2) Date: Jan. 17, 2020

(87) PCT Pub. No.: WO2019/018692
PCT Pub. Date: Jan. 24, 2019

(65) Prior Publication Data
US 2020/0248259 A1   Aug. 6, 2020

Related U.S. Application Data

(60) Provisional application No. 62/534,487, filed on Jul. 19, 2017.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| 5,770,373 A | 6/1998 | Britschgi et al. |
| 2011/0151455 A1 | 6/2011 | Stroot et al. |

(Continued)

OTHER PUBLICATIONS

Cangelosi et al Antimicrobial Agents and Chemotherapy. 1996. 40(8): 1790-1795 (Year: 1996).*

(Continued)

*Primary Examiner* — Carla J Myers
(74) *Attorney, Agent, or Firm* — Saul Ewing LLP; Kathryn Doyle; Domingos J. Silva

(57) ABSTRACT

The present invention provides novel markers of treatment response in a subject infected with *Mycobacterium*, which allow for quantifying treatment impact on the physiologic state of the *Mycobacterium*.

17 Claims, 5 Drawing Sheets

*Mtb* ribosomal operon. Detection of ETS1, ITS1 indicates ongoing rRNA synthesis.

(56) References Cited

U.S. PATENT DOCUMENTS

| | | | |
|---|---|---|---|
| 2014/0256664 A1 | 9/2014 | Houpt et al. | |
| 2016/0160268 A1* | 6/2016 | Haake | C12Q 1/689 506/9 |
| 2016/0377602 A1 | 12/2016 | Palmer et al. | |

OTHER PUBLICATIONS

Weigel et al PLoS ONE. 2013. 8(1): 354886, p. 1-8 (Year: 2013).*

D'Ambrosio et al European Respiration Society. 2015. 1:00010-2015, p. 1-15 (Year: 2015).*

"Assessment of a daily combined preparation of isoniazid, rifampin, and pyrazinamide in a controlled trial of three 6-month regimens for smear-positive pulmonary tuberculosis.", Singapore Tuberculosis Service/British Medical Research Council. Am Rev Respir Dis; 143, 1991, 707-12.

"Controlled clinical trial of four short-course (6-month) regimens of chemotherapy for treatment of pulmonary tuberculosis. Third report. East African-British Medical Research Councils", Lancet; 2, 1974, 237-40.

International Search Report and Written Opinion dated Sep. 17, 2018 for International Appln. No PCT/US18/042963.

"World Health Organization. Global tuberculosis control: WHO report. Geneva", 2015.

Bhat, et al., "Single molecule detection in nanofluidic digital array enables accurate measurement of DNA copy number", Anal Bioanal Chem; 394, 2009, 457-67.

Brauner, et al., "Distinguishing between resistance, tolerance and persistence to antibiotic treatment", Nat Rev Microbiol; 14, 2016, 320-30.

Burman, W. J., "The hunt for the elusive surrogate marker of streilizing activity in tuberculosis treatment", Am J Resp Crit Care; 167, 2003, 1299-300.

Cangelosi, et al., "Dead or alive: Molecular assessment of microbial viability", Appl Env Microbiol, 80, 2014, 5884-91.

Davies, G. R., "Early clinical development of anti-tuberculosis drugs: science, statistics and sterilizing activity", Tuberculosis, 5;90, 2010, 171-6.

Devonshire, et al., "The use of digital PCR to improve the application of quantitative molecular diagnostic methods for tuberculosis", BMC Infect Dis; 16, 2016, 366.

Didelot, et al., "Multiplex picoliter-droplet digital PCR for quantitative assessment of DNA integrity in clinical samples", Clin Chem; 59, 2013, 815-23.

Doherty, et al., "Biomarkers of disease activity, cure, and relapse in tuberculosis", Clin Chest Med;30, 2009, 783-96.

Duque-Correa, et al., "Macrophage arginase-1 controls bacterial growth and pathology in hypoxic tuberculosis granulomas", Proc Nat Acad Sci USA; 111, 2014, E4024-32.

Epand, et al., "Molecular mechanisms of membrane targeting antibiotics", Biochim Biophys Acta, 1858, 2016, 980-7.

Folch, et al., "A simple method for the isolation and purification of total lipides from animal tissues", J Biol Chem; 226, 1957, 497-509.

Garton, et al., "Cytological and transcript analyses reveal fat and lazy persister-like bacilli in tuberculosis sputum.", PLoS Med; 5, 2009, e75.

Gourse, et al., "rRNA transcription and growth rate-dependent regulation of ribosome synthesis in *Escherichia coli*", Annu Rev Microbiol; 50, 1996, 645-77.

Hayden, et al., "Comparison of droplet digital PCR to real-time PCR for quantitative detection of cytomegalovirus", J Clin Microbiol; 51, 2013, 540-6.

Horne, et al., "Sputum monitoring during tuberculosis treatment for predicting outcome: systematic review and meta-analysis", Lancet Infect Dis;10, 2010.

Jindani, et al., "Bactericidal and sterilizing activities of antituberculosis drugs during the first 14 Days", Am J Resp Crit Care; 167, 2003, 1348-54.

Jindani, et al., "The early bactericidal activity of drugs in patients with pulmonary tuberculosis", Am Rev Respir Dis, 121, 1980, 939-49.

Keren, et al., "Characterization and transcriptome analysis of *Mycobacterium tuberculosis* persisters", mBio; 2, 2011.

Kester, et al., "Persisters and beyond: mechanisms of phenotypic drug resistance and drug tolerance in bacteria", Crit Rev Biochem Mol Biol;49, 2014, 91-101.

Kim, et al., "Persistent persister misperceptions", Front Microbiol; 7, 2016, 2134.

Maitra, et al., "Bacterial growth laws reflect the evolutionary importance of energy efficiency.", Proc Natl Acad Sci U S A, 2015, 406-11.

Malherbe, et al., "Persisting positron emission tomography lesion activity and *Mycobacterium tuberculosis* mRNA after tuberculosis cure", Nat Med; 22, 2016, 1094-100.

Manina, et al., "Stress and host immunity amplify *Mycobacterium tuberculosis* phenotypic heterogeneity and induce nongrowing metabolically active forms", Cell Host Microbe, 17, 2015, 32-46.

Mitchison, D. A., "The Garrod Lecture. Understanding the chemotherapy of tuberculosis—current problems", J Antimicrob Chemother; 29, 1992, 477-93.

Mitnick, C. D., "Tuberculosis pharmacotherapy: strategies to optimize patient care", Expert Opin Pharmacother;10, 2009, 381-401.

Nahid, et al., "Official American Thoracic Society/Centers for Disease Control and Prevention/Infectious Diseases Society of America Clinical Practice Guidelines: Treatment of Drug-Susceptible Tuberculosis", Clin Infect Dis Off Publ Infect Dis Soc Am; 63, 2016, e147-195.

Peterson, et al., "Uncoupling environmental pH and intrabacterial acidification from pyrazinamide susceptibility in *Mycobacterium tuberculosis*", Antimicrob Agents Chemother, 59, 2015, 7320-6.

Phillips, et al., "Limited role of culture conversion for decision-making in individual patient care and for advancing novel regimens to confirmatory clinical trials", BMC Med;14, 2016, 1-11.

Prideaux, et al., "The association between sterilizing activity and drug distribution into tuberculosis lesions", Nat Med; 21, 2015, 1223-7.

Schnappinger, et al., "Transcriptional adaptation of *Mycobacterium tuberculosis* within macrophages: Insights into the phagosomal environment", J Exp Med; 198, 2003, 693-704.

Slayden, et al., "Chapter 15: Analysis of the lipids of *Mycobacterium tuberculosis*", Mycobacterium Tuberc. Protoc. Clifton: Humana Press, 59259-141-7:229, (2001)

Via, et al., "Tuberculous granulomas are hypoxic in guinea pigs, rabbits, and nonhuman primates", Infect Immun; 76, 2008, 2333-40.

Wakamoto, et al., "Dynamic persistence of antibiotic-stressed mycobacteria", Science; 339, 2013, 91-5.

Walter, et al., "Transcriptional adaptation of drug-tolerant *Mycobacterium tuberculosis* during treatment of human tuberculosis", J Infect Dis; 212, 2015, 990-8.

Wayne, L. G., "Synchronized replication of *Mycobacterium tuberculosis*", Infect Immun; 17, 1977, 528-30.

Connolly, "Why is long-term therapy required to cure tuberculosis?", PLoS Med, 4(3):e120, 2007.

Dide-Agossou, et al., "Combination of *Mycobacterium tuberculosis* RS Ratio and CFU Improves the Ability of Murine Efficacy Experiments to Distinguish between Drug Treatments", Antimicrob Agents Chemother 66(4):e0231021, 2021.

Dide-Agossou, et al., "MOVER approximated CV: A tool for quantifying precision in ratiometric droplet digital PCR assays", Pharm Biomed Anal 212:114664, 2022.

Dooley, et al., "Challenges in the clinical assessment of novel tuberculosis drugs", Advanced Drug Delivery Reviews, 102, 116, 2016.

Gillespie, et al., "Four-month moxifloxacin-based regimens fordrug-sensitive tuberculosis", N Engl J Med 371, 1577, 2014.

Gumbo, et al., "Nonclinical models for antituberculosis drug development: a landscape analysis", J. Infect. Dis. 211 Suppl 3, S83, 2015.

Musisi, et al., "Reproducibility of the Ribosomal RNA Synthesis Ratio in Sputum and Association with Markers of *Mycobacterium tuberculosis* Burden", Microbiol Spectr. 9(2):e0048121, 2021.

(56) References Cited

OTHER PUBLICATIONS

Phillips, et al., "An evaluation of culture results during treatment for tuberculosis as surrogate endpoints for treatment failure and relapse", PLoS ONE, 8:e63840, 2013.

Walter, et al., "*Mycobacterium tuberculosis* precursor rRNA as a measure of treatment-shortening activity of drugs and regimens", Nature Communication 12:2899, 2021.

* cited by examiner

*Mtb* ribosomal operon. Detection of ETS1, ITS1 indicates ongoing rRNA synthesis.

METHODS OF EVALUATING TREATMENT EFFICACY AND/OR TREATMENT DURATION IN MYCOBACTERIAL DISEASES

CROSS-REFERENCE TO RELATED APPLICATION

This application is a 35 U.S.C. § 371 national phase application from, and claims priority to, International Application No. PCT/US2018/042963, filed Jul. 19, 2018, and published under PCT Article 21(2) in English, which claims priority under 35 U.S.C. § 119(e) to U.S. Provisional Application No. 62/534,487, filed Jul. 19, 2017, all of which applications are incorporated herein by reference in their entireties.

STATEMENT REGARDING FEDERALLY SPONSORED RESEARCH OR DEVELOPMENT

This invention was made with government support under grant numbers AI135652 and AI127300 awarded by National Institutes of Health. The government has certain rights in the invention.

BACKGROUND OF THE INVENTION

Diseases caused by the bacterial genus mycobacteria are a leading cause of death worldwide. Mycobacteria species are broadly divided into two categories: *Mycobacterium tuberculosis* complex (MTBC) organisms. and non-tuberculous mycobacterial (NTM) organisms.

MTBC cause tuberculosis (TB). Worldwide, an estimated 10.4 million people are sickened with TB, and 1.8 million die each year. TB affects the lung most often, although is capable of affecting nearly any part of the body. TB is spread from person-to-person through the air. Globally, the standard treatment for drug-susceptible TB is a six-month regimen that begins with a two-month course of four antibiotics (isoniazid, rifampin, pyrazinamide and ethambutol; this treatment regime is commonly referred to as "HRZE"), and continues for an additional four months with isoniazid and rifampin alone. Unfortunately, the standard six-month, four-drug treatment regimen has not changed in nearly four decades. This treatment's long duration and complexity is a major challenge for health systems, and may lead to non-adherence to treatment. Globally, the World Health Organization (WHO) estimates that about 10% of patients relapse after treatment completion, causing morbidity or death, enabling TB transmission within communities and generating drug resistance. There is an urgent need for new more efficacious drug regimens that cure TB in a shorter period.

The challenges of TB treatment can be massively compounded when the bacterium is drug-resistant. Multiple drug resistant TB (MDR-TB) is defined as resistance to the two most effective first-line TB drugs: rifampin and isoniazid. The WHO considers the growing incidence of MDR-TB to be a global public health crisis. An estimated 480,000 new MDR-TB cases occur each year. Recommended treatment for MDR-TB includes four to seven antibiotics for 9-24 months, but unfortunately the treatment success rate with these regimens is estimated to be only 52% globally. Extensively drug-resistant TB (XDR-TB) has resistance to not only rifampin and isoniazid, but also three or more of the six classes of second-line drugs. Globally, the treatment success rate with these regimens is estimated to be only 28%. Development of new drugs and drug regimens for treatment of MDR-TB and XDR-TB is an urgent priority.

NTM comprises over 125 species. A subset of NTM species is capable of causing devastating disease, particularly among the elderly or patients with underlying lung damage such as cystic fibrosis or bronchiectasis. NTM can cause lung disease, lymph node swelling, skin disease, or disseminated infection. NTM disease is most commonly associated with species in the *Mycobacterium avium* complex (MAC). Among the most difficult-to-treat NTM disease is caused by *Mycobacterium abscesssus* (Mab). In the U.S., NTM is a more common cause of disease than TB. Even with adherence to months to years of treatment with multiple, often toxic, antimicrobial agents, patients may fail treatment or relapse after completing treatment.

A central challenge for both TB and NTM disease is the current lack of reliable markers measurable early in treatment that accurately indicate the duration of treatment required to achieve durable non-relapsing cure. This has critical implications for both routine clinical care and clinical trials. Currently, the routine care of patients with mycobacterial disease is hamstrung by the current inability to stratify treatment duration. For example, nearly all patients worldwide with drug-susceptible TB receive the same "one size fits all" treatment that lasts six months. However, responses to treatment are heterogeneous. For most of these patients, the standard six month regimen is over-treatment; clinical trials show that up to 80% of patients may be durably cured in 4 months. But the standard six month regimen also undertreats an important subset of patients that relapse after completing six months of treatment. In treating NTM disease, clinicians also face the uncertainty about how much treatment is "enough" and how much is "too much."

Lack of a surrogate marker of treatment effectiveness also impedes clinical trials of new drugs. For both TB and NTM, a central goal is curing disease more quickly. Without a marker of treatment-shortening effectiveness, early-phase trials are hamstrung. For example, in TB drug development, a critically important decision is which candidate drug regimens should move from Phase IIb to Phase III clinical trials. Unfortunately, currently Phase IIb trials estimate treatment efficacy based on sputum culture, which is a $19^{th}$ century technology that fails to accurately the duration of treatment required to prevent relapse. Existing culture-based markers provide imprecise, poorly predictive information with minimal statistical power based on endpoints that are dichotomous or, at best, have limited dynamic range. An early marker that indicates a treatment's capacity to shorten treatment would have a transformative effect on the design and conduct of clinical trials, thereby accelerating new drug development. In summary, development of accurate early marker of treatment effectiveness would have a profound effect on drug development and clinical practice.

There remains a need in the art for methods for assessing efficacy of a given drug therapy for treatment of mycobacterial diseases. Such methods should monitor surrogate markers that accurately correlate with treatment response and/or optimal duration. The present invention addresses and meets this need.

BRIEF SUMMARY OF THE INVENTION

The invention provides a method of evaluating treatment efficacy in a subject with a mycobacterial infection who is being administered a first therapeutic treatment against the mycobacterial infection, the method comprising measuring at least one pre-rRNA/mature rRNA ratio in a biological sample that is obtained from the subject after the subject received the first therapeutic treatment from a given period of time. In certain embodiments, if the measured at least one pre-rRNA/mature rRNA ratio is lower than about a given value, the subject is counseled to continue receiving the first therapeutic treatment. In other embodiments, if the measured at least one pre-rRNA/mature rRNA ratio is equal to or higher than about a given value, the subject is counseled to undergo at least one intervention selected from the group consisting of: receiving a second therapeutic treatment instead of the first therapeutic treatment, receiving a higher dose of the first therapeutic treatment, and receiving the first therapeutic treatment for a longer period of time than the standard treatment protocol for the first therapeutic treatment.

The invention further provides a method of evaluating treatment efficacy in a subject with a mycobacterial infection who is being administered a first therapeutic treatment against the mycobacterial infection, the method comprising measuring at least one pre-rRNA/mature rRNA ratio in a biological sample that is obtained from the subject after the subject received the first therapeutic treatment from a given period of time. In certain embodiments, if the measured at least one pre-rRNA/mature rRNA ratio is lower than a control sample's pre-rRNA/mature rRNA ratio by about a reduction factor, the subject is counseled to continue receiving the first therapeutic treatment. In other embodiments, if the measured at least one pre-rRNA/mature rRNA ratio is not lower than a control sample's pre-rRNA/mature rRNA ratio by about a reduction factor, the subject is counseled to undergo at least one intervention selected from the group consisting of: receiving a second therapeutic treatment instead of the first therapeutic treatment, receiving a higher dose of the first therapeutic treatment, and receiving the first therapeutic treatment for a longer period of time than the standard treatment protocol for the first therapeutic treatment.

The invention further provides a method of determining if a subject infected with a *Mycobacterium* is responsive to a therapeutic treatment, the method comprising measuring the pre-rRNA/mature rRNA ratio in a biological sample from the subject that has been contacted with the therapeutic treatment. In certain embodiments, if the measured ratio is lower than about a given value, the subject is counseled to receive the therapeutic treatment. In other embodiments, if the measured ratio is equal to or higher than about a given value, the subject is counseled to receive another therapeutic treatment.

The invention further provides a method of determining if a subject infected with a *Mycobacterium* is responsive to a therapeutic treatment, the method comprising measuring the pre-rRNA/mature rRNA ratio in a biological sample from the subject (pre-treatment ratio), and measuring the pre-rRNA/mature rRNA ratio in a biological sample from the subject that has been contacted with the therapeutic treatment (post-treatment ratio). In certain embodiments, if the post-treatment ratio is lower than the pre-treatment ratio by about a given reduction factor, the subject is counseled to receive the therapeutic treatment. In other embodiments, if the post-treatment ratio is not lower than the pre-treatment ratio by about a given reduction factor, the subject is counseled to receive another therapeutic treatment.

The invention further provides a method of determining optimal duration of administration of a therapeutic treatment to a subject infected with drug-susceptible *M. tuberculosis*, the method comprising measuring the pre-rRNA/mature rRNA ratio in a biological sample from the subject that has been contacted with the therapeutic treatment. In certain embodiments, if the ratio is lower than about a first value, then the subject is counseled to receive the therapeutic treatment for a first period of time. In other embodiments, if the ratio ranges from about the first value to about a second value, wherein the second value is higher than the first value, then the subject is counseled to receive the therapeutic treatment for a second period of time. In yet other embodiments, if the ratio is higher than about the second value, the subject is counseled to receive the therapeutic treatment for a third period of time. In yet other embodiments, the first period of time is shorter in magnitude than the second period of time, which is shorter in magnitude than the third period of time.

The invention further provides a method of determining optimal duration of administration of a therapeutic treatment to a subject infected with drug-susceptible *M. tuberculosis*, the method comprising measuring the pre-rRNA/mature rRNA ratio in a biological sample from the subject (pre-treatment ratio), and measuring the pre-rRNA/mature rRNA ratio in a biological sample from the subject that has been contacted with the therapeutic treatment (post-treatment ratio). In certain embodiments, if the reduction factor is higher than about a first value, then the subject is counseled to receive the therapeutic treatment for a first period of time. In other embodiments, if the reduction value ranges from about a second value to about the first value, wherein the second value is lower than the first value, then the subject is counseled to receive the therapeutic treatment for a second period of time. In yet other embodiments, if the reduction factor is lower than about the second value, the subject is counseled to receive the therapeutic treatment for a third period of time. In yet other embodiments, the first period of time is shorter in magnitude than the second period of time, which is shorter in magnitude than the third period of time.

The invention further provides a method of determining optimal duration of administration of a therapeutic treatment to a subject infected with multiple-drug-resistant *M. tuberculosis*, the method comprising measuring the pre-rRNA/mature rRNA ratio in a biological sample from the subject that has been contacted with the therapeutic treatment. In certain embodiments, if the ratio is lower than about a first value, the subject is counseled to receive the first therapeutic treatment for a period of about 3 months and the second therapeutic treatment for a period of about 3 months. In other embodiments, if the ratio ranges from about the first value to about a second value, wherein the second value is higher than the first value, the subject is counseled to receive the first therapeutic treatment for a period of about 4 months and the second therapeutic treatment for a period of about 5 months. In yet other embodiments, if the ratio is higher than about the second value, the subject is counseled to receive the therapeutic treatment for a period of about 6 months and the second therapeutic treatment for a period of about 5 months.

The invention further provides a method of determining optimal duration of administration of a therapeutic treatment to a subject infected with multiple-drug-resistant *M. tuberculosis*, the method comprising measuring the pre-rRNA/mature rRNA ratio in a biological sample from the subject (pre-treatment ratio), and measuring the pre-rRNA/mature rRNA ratio in a biological sample from the subject that has been contacted with the therapeutic treatment (post-treatment ratio). In certain embodiments, if the reduction factor is higher than about a first value, the subject is counseled to receive the first therapeutic treatment for a period of about 3 months and the second therapeutic treatment for a period of about 3 months. In other embodiments, if the reduction value ranges from about a second value to about the first value, wherein the second value is lower than the first value, the subject is counseled to receive the first therapeutic treatment for a period of about 4 months and the second therapeutic treatment for a period of about 5 months. In yet other embodiments, if the reduction factor is lower than about the second value, the subject is counseled to receive the therapeutic treatment for a period of about 6 months and the second therapeutic treatment for a period of about 5 months.

In certain embodiments, the therapeutic treatment comprises HRZE.

In certain embodiments, the first treatment comprises kanamycin, moxifloxacin, prothionamide, clofazamine, pyrazinamide, and isoniazid.

In certain embodiments, the second treatment comprises moxifloxacin, clofazamine, pyrazinamide, and ethambutol.

In certain embodiments, if the measured at least one pre-rRNA/mature rRNA ratio is equal to or higher than about the given value, the subject is further administered at least one of the following: (a) the second therapeutic treatment instead of the first therapeutic treatment; (b) a higher dose of the first therapeutic treatment; and (c) the first therapeutic treatment for a longer period of time than the standard treatment protocol for the first therapeutic treatment.

In certain embodiments, if the measured at least one pre-rRNA/mature rRNA ratio is not lower than a control sample's pre-rRNA/mature rRNA ratio by about the reduction factor, the subject is further administered at least one of the following: (a) the second therapeutic treatment instead of the first therapeutic treatment; (b) a higher dose of the first therapeutic treatment; and (c) the first therapeutic treatment for a longer period of time than the standard treatment protocol for the first therapeutic treatment.

In certain embodiments, the control sample is from a responsive subject who did not experience clinical relapse while receiving the first therapeutic treatment.

In certain embodiments, the pre-rRNA is at least one selected from the group consisting of ETS1, ITS1, and ITS2.

In certain embodiments, the mature rRNA is at least one selected from the group consisting of 16S rRNA and 23S rRNA.

In certain embodiments, the pre-rRNA/mature rRNA ratio is at least one selected from the group consisting of ETS1/16S rRNA, ETS1/23S rRNA, ITS1/16S rRNA, ITS1/23S rRNA, ITS2/16S rRNA, and ITS2/23S rRNA.

In certain embodiments, the *Mycobacterium* is selected from the group consisting of *Mycobacterium tuberculosis* complex (MTBC) organism, and non-tuberculous *Mycobacterium* (NTM).

In certain embodiments, the *Mycobacterium* is at least one selected from the group consisting of *M. abscessus, M. arupense, M. asiaticum, M. avium, M. chelonae, M. chimaera, M. cosmeticum, M. gordonae, M. intracellulare, M. kansasii, M. lentiflavum, M. mageritense, M. malmoense, M. neoaurum, M. kubicae, M. szulgai, M. tuberculosis*, and *M. xenopi*.

In certain embodiments, the *Mycobacterium* is *M. tuberculosis*.

In certain embodiments, at least the lung of the subject is infected with the *M. tuberculosis*.

In certain embodiments, the first therapeutic treatment comprises at least one selected from the group consisting of isoniazid, rifampin, streptomycin, clofazimine, pyrazinamide, ethambutol, bedaquiline, levofloxacin, kanamycin, moxifloxacin, rifapentine, pretomanid, delamanid, linezolid, amikacin, capreomycin, rifabutin, and cycloserine.

In certain embodiments, the second therapeutic treatment comprises at least one selected from the group consisting of isoniazid, rifampin, streptomycin, clofazimine, pyrazinamide, ethambutol, bedaquiline, levofloxacin, kanamycin, moxifloxacin, rifapentine, pretomanid, delamanid, linezolid, amikacin, capreomycin, rifabutin, and cycloserine.

In certain embodiments, the biological sample comprises at least one selected from the group consisting of sputum, saliva, bronchoalveolar lavage fluid, lung tissue and lymph node tissue. In other embodiments, the biological sample comprises sputum.

In certain embodiments, the measuring of the pre-rRNA/mature rRNA ratio comprises at least one method selected from the group consisting of RNAseq, qRT-PCR, Nanostring, and droplet digital PCR.

In certain embodiments, the subject is a mammal. In other embodiments, the mammal is human.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

DETAILED DESCRIPTION OF THE INVENTION

The present disclosure provides methods for making treatment decisions, and/or evaluating/quantifying treatment efficacy, in *Mycobacterium* diseases. The present disclosure further provides methods for determining duration of treatment required and/or determining the composition of drug regimens for treating mycobacterial diseases. In certain embodiments, the methods comprise performing a ratiometric measure of a fundamental aspect of mycobacterial physiology: the rate of mycobacterial ribosomal RNA (rRNA) synthesis in a biologic sample.

Figure 1:
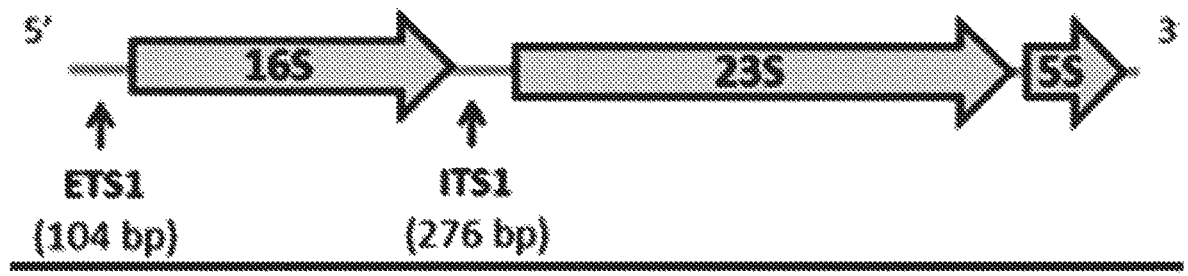
FIG. 1 is a diagram illustrating the *M. tuberculosis* ribosomal operon. Abundance of pre-rRNA (ETS1, ITS1, and ITS2) indicates rRNA synthesis rate.

In one aspect, the present invention comprises estimating and/or quantifying non-coding precursor-rRNA (pre-rRNA), which is an intermediate precursor RNA that is transiently present during rRNA synthesis. Mycobacteria synthesize a single polycistronic pre-rRNA transcript with external and internal transcribed spacers (ETS1, ITS1, ITS2) (FIG. 1). Since ETS1, ITS1, ITS2 are rapidly degraded, abundance of ETS1, ITS1 and ITS2 is proportional to the rRNA synthesis rate.

In one aspect, the present disclosure contemplates measuring and/or estimating a pre-rRNA to mature rRNA ratio (also indicated as pre-rRNA/mature rRNA ratio). In certain embodiments, the present disclosure contemplates this ratiometric analysis because a pre-rRNA/mature rRNA ratio internally controls (normalizes for) for between-sample difference in mycobacterial abundance.

In certain embodiments, the method comprises measuring at least one pre-rRNA/mature rRNA ratio in a subject's biological sample. Specific ratios contemplated within the invention include, but are not limited to: ratio of ETS1 to 16S rRNA; ratio of ETS1 to 23S rRNA; ratio of ITS1 to 16S rRNA; ratio of ITS1 to 23S rRNA; ratio of ITS2 to 16S rRNA; and ratio of ITS2 to 23S rRNA.

In certain embodiments, the method comprises combining two or more of the individual ratios contemplated herein to achieve a single composite pre-rRNA/mature rRNA ratio. As used herein, the term "pre-rRNA ratio" refers to any of the individual pre-rRNA/mature rRNA ratios and/or any of the composite pre-rRNA/mature rRNA ratios contemplated herein.

In certain embodiments, the method comprises measuring or determining a "reduction factor" for at least one pre-rRNA/mature rRNA ratio in a subject's biological sample, wherein the pre-rRNA/mature rRNA ratio is determined at some treatment time and also determined at pre-treatment baseline value. The "reduction factor," as used herein, is defined as the pre-rRNA/mature rRNA ratio determined at pre-treatment baseline value divided by the pre-rRNA/mature rRNA ratio determined at some treatment time In one aspect, the rate of rRNA synthesis directly correlates with the rate of bacterial replication. The experimental data presented in the present disclosure demonstrate that pre-rRNA ratios (which are a measure of the rate of rRNA synthesis) are closely associated with rates of bacterial replication.

The prior art measurements of treatment efficacy are based exclusively on enumeration of the bacterial load or burden in biological samples. By contrast, the method disclosed herein characterizes the physiologic state of mycobacterial populations in biological samples. Without wishing to be limited by any theory, the present invention helps establish a paradigm shift for mycobacterial diseases, away from culture-based metrics of bacillary load, and towards a model in which treatment duration and drug regimens are selected based on markers of drug impact on the pathogen's physiologic state.

In one aspect, the present invention allows for quantifying a drug's "sterilizing" (i.e., treatment-shortening) activity. Anti-mycobacterial treatment has two key phases. The early bactericidal phase (first 3-5 days) of treatment typically kills >99% of mycobacteria. The subsequent months of treatment needed for reliable cure have historically been called the sterilizing phase. Treatment effectiveness during the sterilizing phase determines the total duration needed to achieve durable non-relapsing cure. Efficacious sterilizing activity thus correlates with treatment-shortening activity. At present, there is no existing marker of a drug's treatment-shortening activity. The present invention provides a method of quantifying the effectiveness of drug therapy during the sterilizing phase. This will enable patient-centered tailoring of treatment duration, and/or enable selection of regimens with highest potency during the critical sterilizing phase.

In one aspect, the present invention represents a novel paradigm for understanding and treating mycobacterial diseases. A central challenge in the field is that drug activity during the sterilizing phase is currently neither mechanistically explicable nor easily quantifiable. Decades of human clinical trials demonstrate that the ability of a drug to kill at the start of treatment (bactericidal activity) and the ability to shorten treatment (sterilizing activity) are separate and distinct properties. For example, isoniazid and streptomycin have potent bactericidal activity but have minimal treatment-shortening activity. Other drugs, including rifampin, bedaquiline, and pyrazinamide, have variable bactericidal activity but potent activity in the sterilizing phase, thereby enabling cure with shorter treatment durations. An enduring uncertainty in the field is the molecular basis of drug effectiveness during the sterilizing phase. The present invention provides an explanation and a marker for why drugs vary greatly in their potency during the sterilizing phase.

Based on the experimental data presented herein, the present disclosure contemplates a non-limiting paradigm: that treatment-shortening activity correlates with a drug's capacity to interrupt rRNA synthesis and abrogate mycobacterial replication.

In certain embodiments, pre-rRNA ratios (including reduction factors thereof) measure drug effectiveness during the sterilizing phase. The in vitro, murine and human clinical data presented herein indicate that drugs known to shorten treatment cause massive decreases in pre-rRNA ratios, indicating abrogation of replication. By contrast, drugs that have bactericidal activity, but minimal or no sterilizing activity, do not meaningfully decrease pre-rRNA ratios.

In certain embodiments, the present data indicate that pre-rRNA ratios (including reduction factors thereof) are a marker of treatment-shortening effect. During drug treatment, lower pre-rRNA ratios indicate more effective inhibition of replication and correspondingly superior activity during the sterilizing phase. Higher pre-rRNA ratios indicate continuing bacterial replication and correspondingly inferior activity during the sterilizing phase. As effectiveness during the sterilizing phase is necessary for treatment success and avoidance of relapse, pre-rRNA ratios are associated meaningful patient outcomes.

In certain embodiments, pre-rRNA ratios (including reduction factors thereof) can be used to stratify the duration of drug treatment. Patients found to have low pre-rRNA ratios early in the sterilizing phase can achieve durable non-relapsing cure more rapidly than patients with higher pre-rRNA ratios. This use of the current invention will enable patient-centered stratification of treatment duration, thereby decreasing the problem of under- or over-treatment.

In certain embodiments, pre-rRNA ratios (including reduction factors thereof) are a marker that direct selection of optimal drug regimens. Low pre-rRNA ratios early in the sterilizing phase signal that a regimen is effective and likely to lead to cure. Conversely, higher pre-rRNA ratios early in the sterilizing phase signal less-than-optimal treatment effectiveness and prompt intensification of drug treatment. This use of the current invention enables patient-centered stratification of regimen composition, thereby enabling the appropriate treatment for the patient.

In certain embodiments, pre-rRNA ratios (including reduction factors thereof) can be used for new drug development. Pre-rRNA ratios (including reduction factors thereof) can be used at a pre-clinical stage (in vitro and animal experiments) and in human studies to gauge the treatment-shortening potency of a drug or drug regimen.

In certain embodiments, pre-rRNA ratios (including reduction factors thereof) are quantified in sputa. In other embodiments, pre-rRNA ratios (including reduction factors thereof) provide a tool for characterizing mycobacterial phenotypes and drug responses both in vitro and in complex paucibacillary in vivo environments. In yet other embodiments, bacterial activity and replication in diverse tissue micro-environments can be measured in animal models and natural hosts.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, specific materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "drug-susceptible M. tuberculosis" refers to M. tuberculosis that lacks resistance to the four first-line drugs in HRZE. Drug resistance is measured by any phenotypic genotypic methods that are standard in the medical and/or anti-infective field.

As used herein, the term "multiple-drug-resistant M. tuberculosis" refers to M. tuberculosis that has either phenotypic and/or genotypic resistance to both isoniazid and rifampin. Drug resistance is measured by any phenotypic genotypic methods that are standard in the medical and/or anti-infective field.

As used herein, the term "effective amount" means the amount required to reduce or improve at least one symptom of a disease relative to an untreated patient. The effective amount of an active compound(s) used for therapeutic treatment of a disease varies depending upon the manner of administration, the age, body weight, and general health of the subject.

The phrase "inhibit," as used herein, means to reduce a molecule, a reaction, an interaction, a gene and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein or a gene's stability, expression, function and activity, e.g., antagonists.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Each carrier must be "acceptable" in the sense of being compatible with the other ingredients of the formulation, including the compound useful within the invention, and not injurious to the patient. Examples of materials that can serve as pharmaceutically acceptable carriers are known in the art. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the terms "prevent," "preventing," "prevention," and the like refer to reducing the probability of developing a disorder or condition in a subject, who does not have, but is at risk of or susceptible to developing a disorder or condition.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "therapeutically effective amount" is an amount of a compound of the invention, that when administered to a patient, treats, minimizes and/or ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, the term "treatment" or "treating" is defined as the application or administration of a therapeutic agent, i.e., a compound useful within the invention (alone or in combination with another pharmaceutical agent), to a subject, or application or administration of a therapeutic agent to an isolated tissue or cell line from a subject (e.g., for diagnosis or ex vivo applications), who has a *Mycobacterium* infection and/or disease, a symptom of a *Mycobacterium* infection and/or disease or the potential to develop a *Mycobacterium* infection and/or disease, with the purpose to cure, heal, alleviate, relieve, alter, remedy, ameliorate, improve or affect TB, the symptoms of a *Mycobacterium* infection and/or disease or the potential to develop a *Mycobacterium* infection and/or disease. Such treatments may be specifically tailored or modified, based on knowledge obtained from the field of pharmacogenomics.

Abbreviations used herein include: BPaL—a drug regimen consisting of bedaquiline, pretonamid, and linezolid; HRZE—the global standard treatment regimen consisting of isoniazid, rifampin, pyrazinamide, and ethambutol; MDR-TB—multiple drug resistant tuberculosis; MTBC—*Mycobacterium tuberculosis* complex organism; NTM—non-tuberculous *Mycobacterium*; TB—tuberculosis; XDR-TB—extensively drug-resistant tuberculosis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

Methods

The invention provides a method of evaluating, monitoring and/or optimizing treatment regimens for mycobacterial disease based on ratiometric measure of pre-rRNA abundance. The invention further provides a method of evaluating, monitoring and/or optimizing treatment duration and regimen composition for mycobacterial disease based on ratiometric measure of pre-rRNA abundance. In certain embodiments, the method comprises measuring at least one pre-rRNA/mature rRNA ratio in a subject's biological sample.

In certain embodiments, the sample is obtained at about 0 weeks of treatment (no significant treatment, or no treatment at all). In other embodiments, the sample is obtained at about 1 week of treatment. In yet other embodiments, the sample is obtained at about 2 weeks of treatment. In yet other embodiments, the sample is obtained at about 3 weeks of treatment. In yet other embodiments, the sample is obtained at about 4 weeks of treatment. In yet other embodiments, the sample is obtained at about 5 weeks of treatment. In yet other embodiments, the sample is obtained at about 6 weeks of treatment. In yet other embodiments, the sample is obtained at about 7 weeks of treatment. In yet other embodiments, the sample is obtained at about 8 weeks of treatment. In yet other embodiments, the sample is obtained at about 9 weeks of treatment. In yet other embodiments, the sample is obtained at about 10 weeks of treatment. In yet other embodiments, the sample is obtained at about 11 weeks of treatment. In yet other embodiments, the sample is obtained at about 12 weeks of treatment. In yet other embodiments, the sample is obtained at about 13 weeks of treatment. In yet other embodiments, the sample is obtained at about 14 weeks of treatment. In yet other embodiments, the sample is obtained at about 15 weeks of treatment. In yet other embodiments, the sample is obtained at about 16 weeks of treatment. In yet other embodiments, the sample is obtained at about 16 weeks or more of treatment.

In yet other embodiments, the pre-rRNA/mature rRNA ratio is selected from the group consisting of $1.5 \times 10^{-4}$, $2 \times 10^{-4}$, $2.5 \times 10^{-4}$, $3 \times 10^{-4}$, $4 \times 10^{-4}$, $5 \times 10^{-4}$, $6 \times 10^{-4}$, $7 \times 10^{-4}$, $8 \times 10^{-4}$, $9 \times 10^{-4}$, $10 \times 10^{-4}$, $20 \times 10^{-4}$, $30 \times 10^{-4}$, $40 \times 10^{-4}$, $50 \times 10^{-4}$, $60 \times 10^{-4}$, $70 \times 10^{-4}$, $80 \times 10^{-4}$, $90 \times 10^{-4}$, $100 \times 10^{-4}$, $150 \times 10^{-4}$, $200 \times 10^{-4}$, $250 \times 10^{-4}$, $300 \times 10^{-4}$, $350 \times 10^{-4}$, $400 \times 10^{-4}$, $450 \times 10^{-4}$, $500 \times 10^{-4}$, $550 \times 10^{-4}$, $600 \times 10^{-4}$, $650 \times 10^{-4}$, $700 \times 10^{-4}$, $750 \times 10^{-4}$, $800 \times 10^{-4}$, $850 \times 10^{-4}$, $900 \times 10^{-4}$, $950 \times 10^{-4}$, $1,000 \times 10^{-4}$, and greater than $1,000 \times 10^{-4}$. In yet other embodiments, the ratio is selected from the group consisting of $19 \times 10^{-4}$, $30.5 \times 10^{-4}$, $46.2 \times 10^{-4}$, $57.4 \times 10^{-4}$, $61.5 \times 10^{-4}$, $85.5 \times 10^{-4}$, $154.8 \times 10^{-4}$, and $214.5 \times 10^{-4}$. In yet other embodiments, the ratio is equal to or greater than about $19 \times 10^{-4}$. In yet other embodiments, the ratio is equal to or greater than about $30.5 \times 10^{-4}$. In yet other embodiments, the ratio is equal to or greater than about $46.2 \times 10^{-4}$. In yet other embodiments, the ratio is equal to or greater than about $57.4 \times 10^{-4}$. In yet other embodiments, the ratio is equal to or greater than about $61.5 \times 10^{-4}$. In yet other embodiments, the ratio is equal to or greater than about $85.5 \times 10^{-4}$. In yet other embodiments, the ratio is equal to or greater than about $154.8 \times 10^{-4}$. In yet other embodiments, the ratio is equal to or greater than about $214.5 \times 10^{-4}$. In yet other embodiments, the ratio is equal to or less than about $19 \times 10^{-4}$. In yet other embodiments, the ratio is equal to or less than about $30.5 \times 10^{-4}$. In yet other embodiments, the ratio is equal to or less than about $46.2 \times 10^{-4}$. In yet other embodiments, the ratio is equal to or less than about $57.4 \times 10^{-4}$. In yet other embodiments, the ratio is equal to or less than about $61.5 \times 10^{-4}$. In yet other embodiments, the ratio is equal to or less than about $85.5 \times 10^{-4}$. In yet other embodiments, the ratio is equal to or less than about $154.8 \times 10^{-4}$. In yet other embodiments, the ratio is equal to or less than about $214.5 \times 10^{-4}$.

In certain embodiments, the ratio is equal to or lower than about $30.5 \times 10^{-4}$. In other embodiments, the ratio ranges from about $30.5 \times 10^{-4}$ to about $61.5 \times 10^{-4}$. In yet other embodiments, the ratio is equal to or greater than about $61.5 \times 10^{-4}$. In yet other embodiments, the ratio is equal to or lower than about $85.5 \times 10^{-4}$. In yet other embodiments, the ratio ranges from about $85.5 \times 10^{-4}$ to about $214.5 \times 10^{-4}$. In yet other embodiments, the ratio is equal to or greater than about $214.5 \times 10^{-4}$. In yet other embodiments, the ratio is equal to or lower than about $19.0 \times 10^{-4}$. In yet other embodiments, the ratio ranges from about $19.0 \times 10^{-4}$ to about $57.4 \times 10^{-4}$. In yet other embodiments, the ratio is equal to or greater than about $57.4 \times 10^{-4}$. In yet other embodiments, the ratio is equal to or lower than about $46.2 \times 10^{-4}$. In yet other embodiments, the ratio ranges from about $46.2 \times 10^{-4}$ to about $154.8 \times 10^{-4}$. In yet other embodiments, the ratio is equal to or greater than about $154.8 \times 10^{-4}$.

In certain embodiments, the at least one pre-rRNA ratio obtained after treatment is administered for a certain time period (on-treatment) is compared in that ratio of a biological sample obtained prior to initiation of drug treatment (pre-treatment).

In certain embodiments, the invention contemplates calculating a reduction factor corresponding to the inverse of the fraction [on-treatment ratio/pre-treatment ratio]. So if the reduction factor is 2, that means that the on-treatment ratio is 1/2 (50%) of the pre-treatment ratio. If the reduction factor is 10, that means that the on-treatment ratio is 1/10 (10%) of the pre-treatment ratio.

In certain embodiments, if the reduction factor is lower than a certain threshold value (indicating less-than-optimal decrease in ratios), drug treatment is extended for a certain duration beyond the standard treatment length. In other embodiments, if the reduction factor is lower than a certain threshold value, an existing drug treatment is changed by either increasing dose or changing to an alternative drug regimen. In yet other embodiments, the reduction factor is selected from the group consisting of 1.5, 2, 2.5, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1,000, and greater than 1,000. In yet other embodiments, the reduction factor is 2. In yet other embodiments, the reduction factor is equal to or greater than about 3.5. In yet other embodiments, the reduction factor is equal to or greater than about 5.6. In yet other embodiments, the reduction factor is equal to or greater than about 14.0. In yet other embodiments, the reduction factor is equal to or greater than about 15.5. In yet other embodiments, the reduction factor is equal to or greater than about 19.6. In yet other embodiments, the reduction factor is equal to or greater than about 24.1. In yet other embodiments, the reduction factor is equal to or greater than about 33.9. In yet other embodiments, the reduction factor is equal to or greater than about 57.4. In yet other embodiments, the reduction factor is equal to or less than about 3.5. In yet other embodiments, the reduction factor is equal to or less than about 5.6. In yet other embodiments, the reduction factor is equal to or less than about 14.0. In yet other embodiments, the reduction factor is equal to or less than about 15.5. In yet other embodiments, the reduction factor is equal to or less than about 19.6. In yet other embodiments, the reduction factor is equal to or less than about 24.1. In yet other embodiments, the reduction factor is equal to or less than about 33.9. In yet other embodiments, the reduction factor is equal to or less than about 57.4.

In certain embodiments, the reduction factor is equal to or greater than about 33.9. In other embodiments, the reduction factor ranges from about 14.0 to about 33.9. In yet other embodiments, the reduction factor is equal to or lower than about 14.0. In yet other embodiments, the reduction factor is equal to or greater than about 15.5. In yet other embodiments, the reduction factor ranges from about 3.5 to about 15.5. In yet other embodiments, the reduction factor is equal to or lower than about 3.5. In yet other embodiments, the reduction factor is equal to or greater than about 57.4. In yet other embodiments, the reduction factor ranges from about 19.6 to about 57.4. In yet other embodiments, the reduction factor is equal to or lower than about 19.6. In yet other embodiments, the reduction factor is equal to or greater than about 24.1. In yet other embodiments, the reduction factor ranges from about 5.6 to about 24.1. In yet other embodiments, the reduction factor is equal to or lower than about 5.6.

In certain embodiments, the measured at least one pre-rRNA ratio is compared to a reference ratio derived from a control sample. In other embodiments, the reference ratio is derived from clinical studies of human patients who were treated for the same bacterial disease and who did not experience relapse during treatment. In yet other embodiments, the reference ratio is based on experimental drug exposures in animals or in in vitro culture.

In certain embodiments, the at least one pre-rRNA ratio is combined with measurement of abundance of 16S or 23S rRNA to create a combined ratiometric/abundance measurement. This combined ratiometric/abundance measurement obtained after treatment is administered for a certain time period can be compared to that from a clinical sample obtained prior to initiation of drug treatment. Alternatively, this combined ratiometric/abundance measurement obtained after treatment is administered for a certain time period can be compared to that from a reference sample.

In certain embodiments, the biological sample comprises sputum, saliva, bronchoalveolar lavage fluid, lung tissue and/or lymph node tissue.

In certain embodiments, the measuring of ETS1, ITS1, ITS2 and 23S rRNA comprises at least one method selected from the group consisting of RNAseq, qRT-PCR, Nanostring and droplet digital PCR.

In certain embodiments, the subject is a mammal. In other embodiments, the subject is human.

Administration/Dosage/Formulations

The regimen of administration may affect what constitutes an effective amount. The therapeutic formulations may be administered to the subject either prior to or after the onset of a disease or disorder contemplated in the invention.

Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent (i.e., capable of treating TB) in the composition. In yet other embodiments, the compound of the invention is the only biologically active agent (i.e., capable of treating TB) in therapeutically effective amounts in the composition.

It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Routes of administration of any of the compositions of the invention include oral nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-peritoneal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Dosing

The therapeutically effective amount or dose of a compound of the present invention depends on the age and weight of the patient, the current medical condition of the patient and the progression of a disease or disorder contemplated in the invention. The skilled artisan is able to determine appropriate dosages depending on these and other factors.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations that become evident as a result of the teaching provided herein.

Example 1

Measurement of Pre-rRNA

*M. tuberculosis* and *M. abscessus* re-rRNA and rRNA were assayed in three different labs using three platforms: RNAseq, qRT-PCR (TaqMan) and droplet digital PCR (ddPCR). A series of experiments were conducted to assure specificity of PCR primer/probe sets in order to avoid non-specific amplification. The PCR primer/probe sets for *M. tuberculosis* ETS1, ITS1 and 23S were validated by testing DNA from *M. gordonae, M. avium, M. xenopi, M. szulgai, M. lentiflavum, M. neoaurum, M. mageritense, M. chelonae, M. cosmeticum, M. abscessus* and human. The PCR primer/probe sets for *M. abscessus* ETS1, ITS1 and 23S were validated by testing DNA from *M. chimaera, M. avium, M. intracellulare, M. chelonae, M. asiaticum, M. arupense, M. kansasii, M. kubicae, M. gordonae, M. malmoense, M. avium hominissuis, M. tuberculosis* and human. No significant off-target detection was found. Primer/probe sets for *M. abscessus* were confirmed that amplify all *M. abscessus* subspecies by testing DNA from *M. abscessus*, subspecies *massiliense, M. abscessus*, subspecies *abscessus*, and *M. abscessus*, subspecies *bolletii*.

Figure 2:
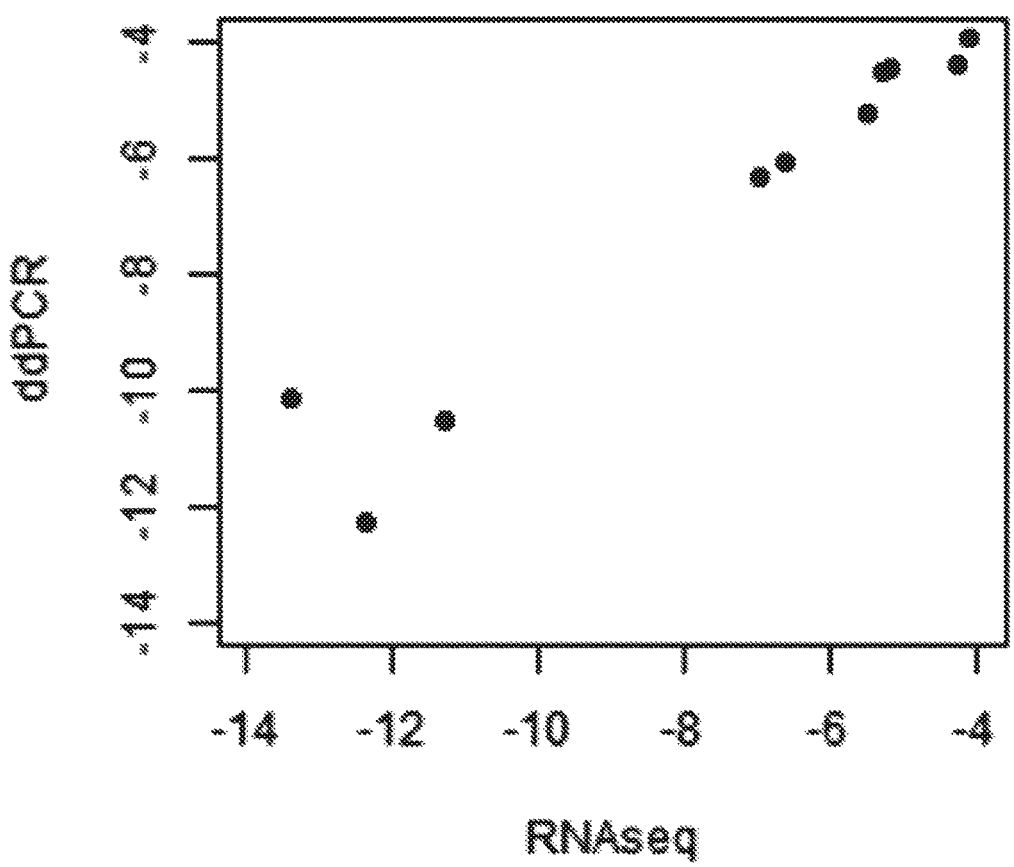
FIG. 2 is a graph illustrating a measurement of the correlation $\log_2$ (ETS1/23S) by RNAseq and ddPCR.

In in vitro experiments described herein, measurement of pre-rRNA was highly correlated between platforms. As an example, correlation between *M. tuberculosis* ETS1/23S measured via RNAseq and ddPCR was 0.95 (illustrated on $\log_2$ scale in FIG. 2). Correlation between *M. tuberculosis* ETS1/23S measured via RNAseq and TaqMan qRTPCR was 0.95. Correlation between *M. tuberculosis* ETS1/23S measured via ddPCR and TaqMan qRT-PCR was 0.99. Between-platform correlation was similarly high for other pre-rRNA ratios and *M. abscessus*.

An additional measure of data validity is testing whether concentration of ETS1 and concentration of ITS1 are closely correlated in individual samples. Conceptually, ETS1 and ITS1 should track closely together since they are components of the same biological process: rRNA synthesis. For *M. tuberculosis*, correlation of $\log_{10}$ ETS1/23S and ITS1/23S (measured via qRT-PCR) was 0.95 in in vitro experiments and 0.88 in sputa. These findings demonstrated internal consistency.

Example 2

Figure 3:
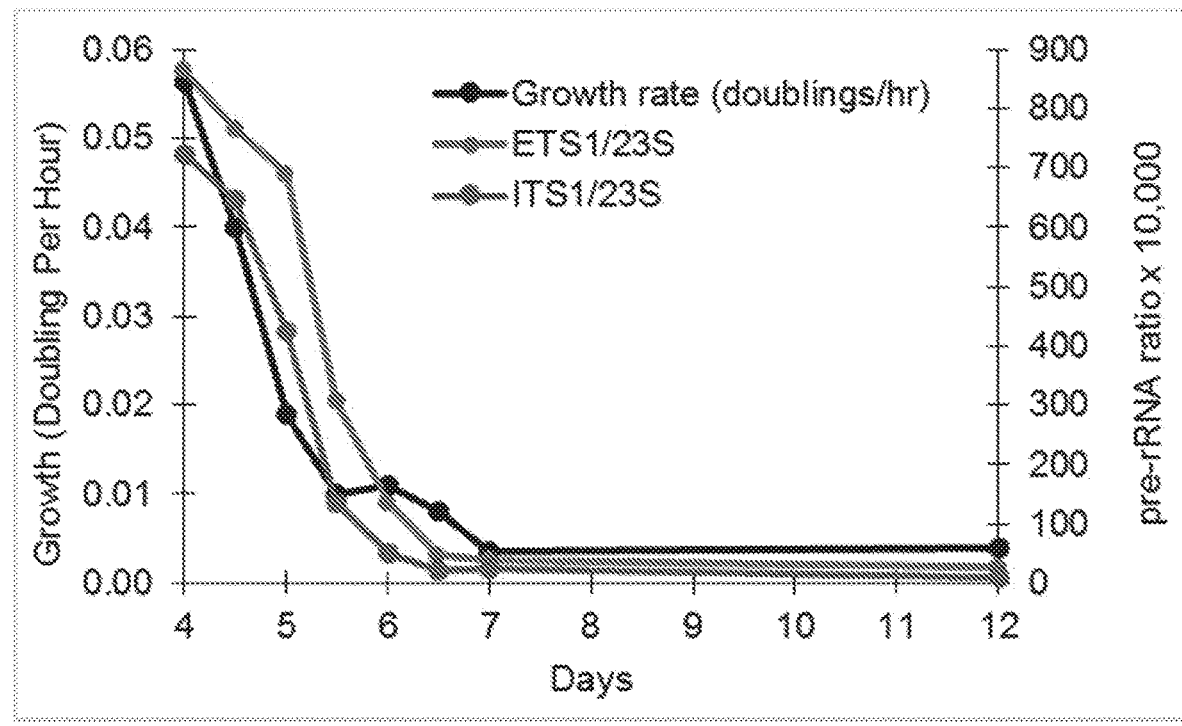
FIG. 3 is a graph illustrating correlation of ETS1/23S and ITS1/23S rRNA ratios ($\times 10^4$) with growth rate in *M tuberculosis* in a standard in vitro oxygen depletion model.

Experimental Evidence that Pre-rRNA Ratios Elucidate Mycobacterial Replication Rate A core microbiologic principle is that rRNA synthesis is directly correlated with bacterial replication. A series of experiments were conducted to validate that pre-rRNA ratios (a measure of rRNA synthesis rate) accurately measure mycobacterial replication rates. Because *M. tuberculosis* requires oxygen for growth, this was demonstrated in vitro in an oxygen depletion model. *M. tuberculosis* Erdman was grown in a capped tube with limited headspace. As oxygen was depleted, replication slowed from 0.056 doublings/hr (doubling time=17.9 hrs) to no growth. ETS1/23S and ITS ratios mirrored growth, decreasing 30-40-fold in the transition from aerobic to anaerobic conditions (FIG. 3). These results show that pre-rRNA ratios are an indirect measure of replication.

Figure 4:
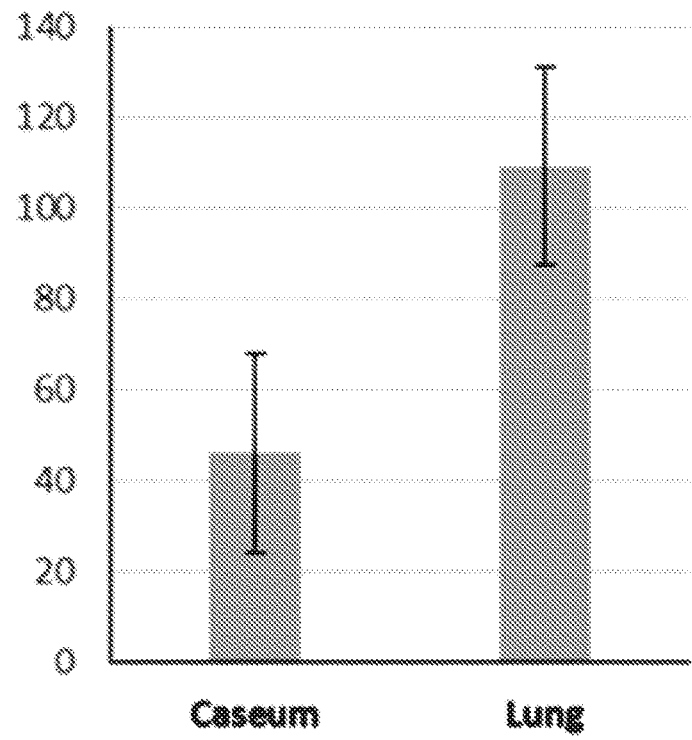
FIG. 4 is a bar graph illustrating ETS1/23S rRNA ratio ($\times 10^4$) from *M. tuberculosis* isolated from primary lesion caseum and whole lung tissue from C3HeB/FeJ "Kramnik" TB mouse models.

Additional experiments were conducted to determine whether pre-rRNA ratios correlate with mycobacterial growth rate in vivo (in the absence of drug exposure). *M. tuberculosis* is known to replicate slowly in the hypoxic microenvironment of granuloma caseum. *M. tuberculosis* pre-rRNA ratios in granuloma caseum were compared versus whole lungs from infected C3HeB/FeJ (Kramnik) mice (a strain that recapitulates the histopathology of human TB). FIG. 4 demonstrates that the ETS1/23S ratio was significantly lower in caseum (p=0.01) than whole lung. The ability to discern this difference is remarkable, since whole lung is a mixture of granuloma and non-lesional tissue. These in vitro and mouse experiments demonstrate that pre-rRNA ratios accurately indicate mycobacterial replication rate.

Example 3

Effect of Treatment-Shortening and Non-Treatment-Shortening Drugs on Pre-rRNA Ratios In Vitro In one aspect, the present disclosure contemplates measuring drug effect on pre-rRNA ratios. A series of experiments tested impact of drug exposure on pre-rRNA ratios in vitro. These experiments exposed *M. tuberculosis* Erdman strain growing at log phase in culture to lethal doses of various antibiotics. After 99.9% of a bacterial population is killed, the surviving residual subpopulation withstands killing despite an absence of resistance-conferring mutations. In these experiments, 48 h of exposure to rifampin, isoniazid or streptomycin killed 99.99% of *M. tuberculosis*; 48 h exposure to bedaquiline killed ~99.9%. RNA was extracted and pre-rRNA ratios were determined via ddPCR and RNAseq.

Figure 5:
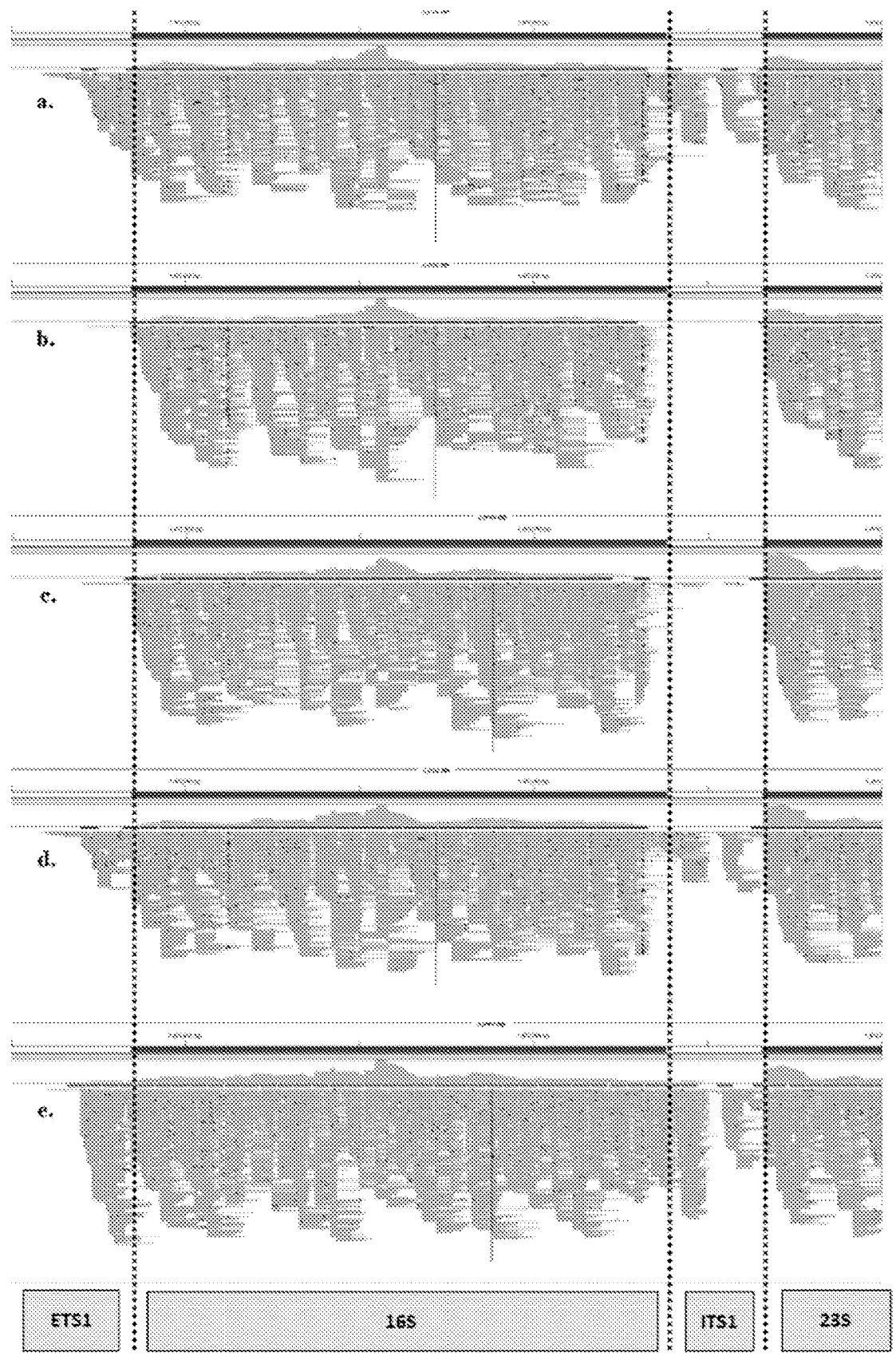
FIG. 5 illustrates an IGV screenshot of RNAseq data from in vitro drug exposures. Dotted lines mark ETS1, 16S, ITS1 & 23S sequence. Lines denote individual reads. Pre-rRNA was present in log phase drug-unexposed control (panel a) indicating ongoing rRNA synthesis. *M tuberculosis* that survived 48 h lethal exposure of rifampin (panel b) or bedaquiline (panel c) had negligible pre-rRNA, indicating abrogation of rRNA synthesis. *M tuberculosis* that survived 48 h lethal isoniazid exposure (panel d) or streptomycin (panel e) had abundant pre-rRNA, indicating continuing rRNA synthesis.

Drug impact on pre-rRNA ratios varied markedly between treatment-shortening (i.e., sterilizing) drugs such as rifampin and bedaquiline and non-treatment shortening (i.e., non-sterilizing) drugs such as isoniazid and streptomycin. Consistent with its mechanism of action (inhibition of RNA polymerase), 48 h of rifampin exposure nearly complete abrogated ETS1 and ITS1 (FIG. 5, panel b), relative to control (FIG. 5, panel a). ETS1/23S and ITS1/23S decreased >100-fold (Table 1). Bedaquiline, a sterilizing drug that inhibits *M. tuberculosis* ATP synthase (without directly inhibiting RNA synthesis), decreased ETS1/23S and ITS1/23S>20-fold (FIG. 5, panel c, Table 1). Conversely, lethal exposure to isoniazid (a non-sterilizing drug that inhibits synthesis of cell wall mycolic acids) decreased ETS1/23S and ITS1/23S only ~50%, consistent with continued replication (since non-replicating bacteria do not require significant ribosome synthesis). Lethal doses of streptomycin, a non-sterilizing antibiotic that inhibits 30S ribosomal function, increased ETS1 and ITS1 (FIG. 5, panel e, Table 1), likely as a compensatory response to sustain ribosomal function. In summary, the treatment-shortening drugs tested profoundly suppressed pre-rRNA ratios. Non-treatment shortening drugs did not suppress pre-rRNA ratios, indicating continuing active rRNA synthesis.

TABLE 1

RNAseq results. Normalized *M. tuberculosis* ETS1, ITS1, 16S, and 23S counts during highly lethal in vitro drug exposure illustrate marked decline in ETS1 and ITS1 with treatment-shortening (rifampin, bedaquiline) but not non-treatment-shortening (isoniazid, streptomycin) drugs.

| | Control | Rifampin | | Bedaquiline | | Isoniazid | | Streptomycin | |
|---|---|---|---|---|---|---|---|---|---|
| | | Day 2 | Day 5 | Day 2 | Day 7 | Day 2 | Day 7 | Day 2 | Day 5 |
| Transcripts per Million (TPM) | | | | | | | | | |
| 16S | 417,822 | 375,111 | 306,538 | 343,978 | 208,644 | 423,197 | 451,670 | 453,930 | 406,987 |
| 23S | 530,225 | 624,759 | 693,196 | 654,924 | 788,154 | 556,210 | 519,579 | 430,311 | 488,000 |
| ETS1 | 27,258 | 58 | 30 | 548 | 1,778 | 12,092 | 16,987 | 78,749 | 72,994 |
| ITS1 | 24,695 | 72 | 235 | 551 | 1,425 | 8,502 | 11,763 | 37,010 | 32,019 |
| Pre-RNA/23S ($\times 10^4$) | | | | | | | | | |
| ETS1/23S | 514 | 0.92 | 0.44 | 8.4 | 22.6 | 217 | 327 | 1,830 | 1,496 |
| ITS1/23S | 466 | 1.15 | 3.39 | 8.4 | 18.1 | 153 | 226 | 860 | 656 |

Example 4

Association Between Treatment-Shortening Activity and Pre-rRNA Ratios in Mice

The BALB/c murine TB relapse model is a widely accepted murine tuberculosis model that has demonstrated excellent predictive capacity in assessing the ability of drug regimens to achieve durable cure (i.e., treatment-shortening or sterilizing activity). In this model, mice are administered a treatment regimen then held untreated for 12 weeks before sacrifice. At the time of sacrifice, the proportion of mice with microbiologic relapse indicates the potency of drug regimens during the sterilizing phase. A lower relapse proportion indicates that a regimen cures TB in a shorter period of time.

HRZE, the existing global standard first-line 4-drug regimen, was compared with an experimental regimen that is known to cure TB faster. The experimental regimen is bedaquiline, pretomanid and linezolid (BPaL). In certain non-limiting embodiments, lower pre-rRNA ratios measured early in treatment (after 4 weeks) are associated with lower relapse proportion 12 weeks after treatment completion. In summary, this experiment tested the ability of the biomarker to predict subsequent relapse.

Figure 6:
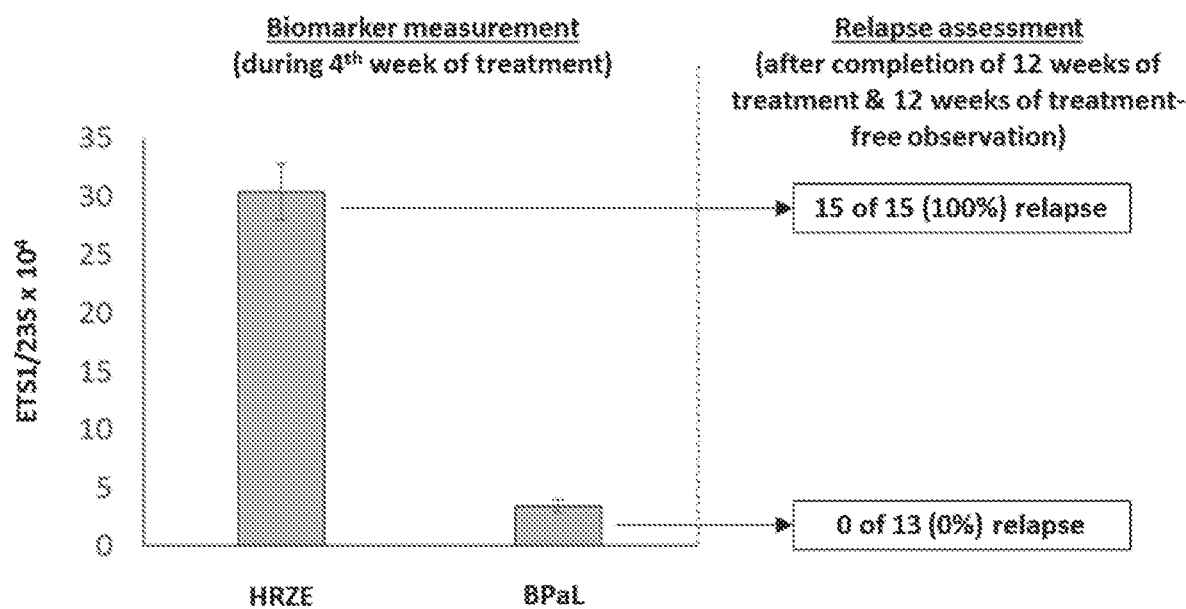
FIG. 6 is a graph illustrating the association between ETS1/23S measured early in treatment (at 4 weeks) with subsequent relapse in BALB/c mice. Comparison of HRZE and an experimental regimen (BPaL) indicated that pre-rRNA/mature rRNA ratios early in treatment are strongly associated with treatment-shortening activity of drug regimens.

BALB/c mice underwent high-dose aerosol infection with *M. tuberculosis* Erdman and were then treated with standard doses of HRZE or BPaL. In each group, 6 mice were sacrificed after 4 weeks. At this early time point, ETS1/23S ratios were 8.9-fold lower with BPaL than with HRZE ((p<0.0001). As illustrated in FIG. 6, the remaining mice completed 12 weeks of treatment and 12 weeks of observation without treatment before sacrifice. With HRZE, 15 of 15 (100%) mice relapsed. With BPaL, 0 of 13 (0%) mice relapsed (p<0.00001). In summary, there was an extremely strong association between ETS1/23S measured early in treatment and subsequent relapse.

Example 5

Pre-rRNA Ratios Declined in Human Sputum During TB Treatment

The clinical studies show that treatment of TB with HRZE profoundly decreases *M. tuberculosis* pre-rRNA ratios in human sputum. The two studies summarized herein demonstrate this in diverse patient populations (Vietnam and Uganda) with diverse *M. tuberculosis* strains.

Figure 7A:
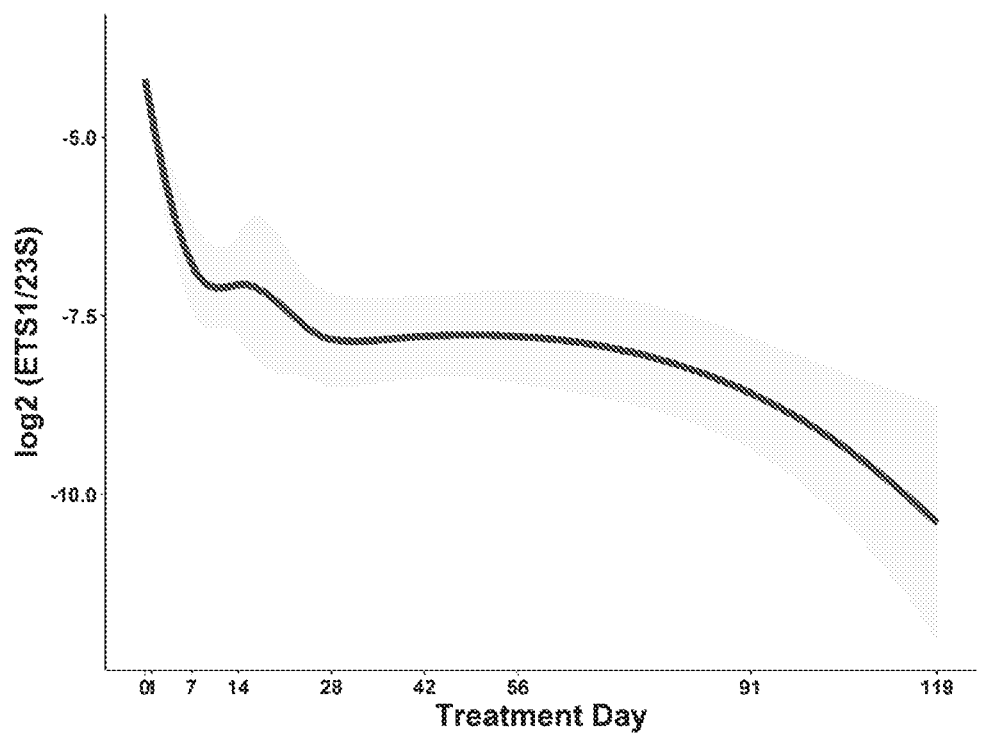
FIG. 7A is a set of graphs illustrating $\log_e$ ratios of ETS1/23S rRNA (top), ITS1/23S rRNA (bottom) among 28 Vietnamese patients treated for drug-susceptible pulmonary TB. Individual patient values in gray dots. Lowess regression line in black.
Figure 7B:
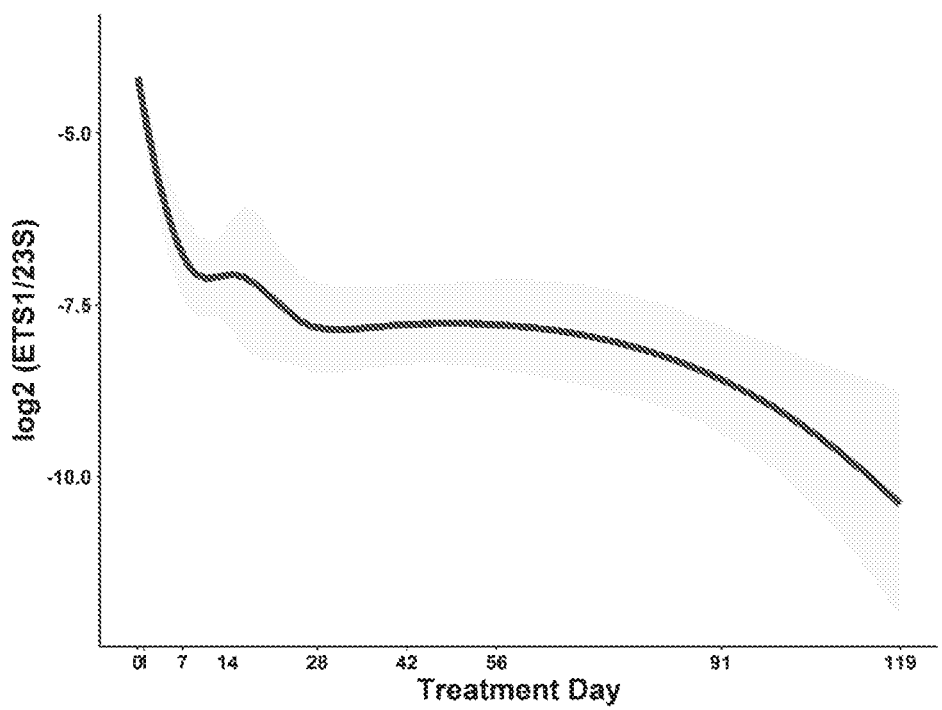
FIG. 7B is a graph illustrating change in ETS1/23S in sputum during treatment of Vietnamese patients. Lines represent individual patient values (scaled to the same baseline value for clarity).

In a first study, serial RNA sputum specimens were obtained from a CDC TB Trials Consortium study at the National Lung Hospital, Hanoi, Vietnam. Patients with drug-susceptible TB expectorated into a GTC solution prior to and after 1, 7, 14, 28, and 56 treatment days. GTC denatures proteins, providing immediate RNA stabilization that is equivalent to snap freezing in liquid nitrogen. Sputum was processed and total RNA extracted using previously documented protocols (Walter, et al., 2015, J. Infect. Dis. 212:990-8). qRT-PCR (TaqMan) was used to profile longitudinal specimens from 28 patients. This demonstrated that ETS1/23S declined with treatment, by 8-fold by day 14 and eventually by >32-fold by day 56 (FIG. 7A).

In a second study, serial RNA sputum specimens were obtained from patients with drug-susceptible TB at Mulago Hospital Complex, Kampala, Uganda. Using procedures identical to those above, forty patients provided sputa with immediate RNA stabilization prior to and after 2, 4, 7, 14, 28, and 56 treatment days. ETS1/23S declined in a manner similar to that observed in Vietnam. The Vietnam and Uganda studies provide normative data from patients successfully treated with the global standard four-drug TB regimen. Pre-rRNA ratios can be tested in large numbers of patients treated with different regimens for drug-susceptible and drug-resistant TB in clinical drug trials, to determine if pre-rRNA ratios accurately predict relapse.

Example 6

Association of Pre-rRNA Ratios with Sputum Culture Status

Sputum culture is the existing standard (but highly problematic) surrogate marker for TB treatment response. Sputum culture does not quantify treatment-shortening (sterilizing) activity and is poorly correlated with patient outcomes. The present invention addresses this need by presenting a marker of treatment-shortening activity. In certain embodiments, the rapidity of growth in sputum culture can be influenced by: (1) the burden of *M. tuberculosis* in sputum (i.e. more *M. tuberculosis* results in shorter time to sputum culture positivity (TTP) in liquid culture) and (2) the replication rate of *M. tuberculosis* at the time of sputum collection (i.e. dormant *M. tuberculosis* phenotypes will grow more slowly, if at all).

For the Vietnamese patients described herein, TTP was thus modeled as a function of either ETS1/23S or ITS1/23S. A longitudinal mixed-effects regression model was used in the SAS NLMIXED procedure to account for repeated measures on the same subject. The first unadjusted models showed that ratios are highly associated with TTP. The second models adjust for *M. tuberculosis* burden (based on 23S copy number) to determine the independent effect of pre-rRNA ratios (Table 2). This demonstrates that—even after accounting for the burden of *M. tuberculosis* present—pre-rRNA ratios are independent predictors of time to growth in culture. It provides further evidence that pre-rRNA ratios provide physiologically meaningful information in vivo. This analysis indicates that pre-rRNA/23S is (1) associated with the existing (imperfect) reference standard and (2) reflects a physiologically important characteristic of *M. tuberculosis*.

TABLE 2

P-values for ETS1/23S and ITS1/23S association with sputum culture positivity and TTP in longitudinal models.

| Model | Outcome | Parameter | p-value |
|---|---|---|---|
| Unadjusted logistic | Sputum culture pos/neg | TTP vs ETS1/23S | 0.0008 |
|  |  | TTP vs ITS1/23S | 0.0004 |
| Adjusted logistic | Sputum culture pos/neg | TTP vs ETS1/23S + 23S | 0.010 |
|  |  | TTP vs ITS1/23S + 23S | 0.032 |
| Unadjusted linear | TTP in liquid culture | TTP vs ETS1/23S | <0.0001 |
|  |  | TTP vs ITS1/23S | <0.0001 |
| Adjusted linear | TTP in liquid culture | TTP vs ETS1/23S + 23S | 0.0035 |
|  |  | TTP vs ITS1/23S + 23S | 0.0022 |

Example 7

Pre-rRNA Ratio Thresholds Used to Direct Drug Administration

Pre-rRNA ratios can be used for at least two clinical purposes: (1) to stratify patients into different risk groups that receive different durations of treatment, and (2) to determine whether additional antibiotics should be added to a treatment regimen. These clinical decisions are made on the basis of a patient's pre-rRNA ratios relative to threshold values. The present disclosure provides two types of thresholds based on: (1) the pre-rRNA ratio at a specified point, and (2) the reduction factor relative to pre-treatment baseline value. The use of these thresholds is presented herein.

In the first iteration, the pre-rRNA ratio can be measured at a specified time point after treatment initiation. For drug-susceptible TB, this is typically one or two months after starting treatment. However, for MDR-TB or non-TB mycobacterial disease, the optimal sampling time could differ. In this first iteration, the pre-rRNA ratio is evaluated without reference to the patient's pre-treatment pre-rRNA ratio. For drug-susceptible TB, Table 3 illustrates the use of pre-rRNA ratios measured 4 and 8 weeks after treatment initiation. These thresholds are based on the cohort of Vietnamese patients treated with HRZE described above in Examples 5 and 6. Based on historical clinical trial indicating that at least 25% of patients are durably cured with 4 months of HRZE, low risk for relapse was defined as pre-rRNA ratio less than the first quartile pre-rRNA ratio at this time point. Similarly, the high risk for relapse group was defined as pre-rRNA ratio greater than the third quartile pre-rRNA ratio at this time point.

TABLE 3

Illustration of the use of pre-rRNA ratios to direct treatment duration or composition of antibiotic regimen for drug-susceptible TB. Pre-rRNA ratios are measured in sputum 4 or 8 weeks after treatment initiation.

|  | ETS1/23S | ITS1/23S | Treatment duration (months) | Antibiotic regimen |
|---|---|---|---|---|
| Week 4 |  |  |  |  |
| Low | ≤30.5 | ≤85.5 | 4 | No change |
| Intermediate | >30.5 and <61.5 | >85.5 and <214.5 | 6 | No change |
| High | ≥61.5 | ≥214.5 | 9 | Add moxifloxacin or clofazamine |
| Week 8 |  |  |  |  |
| Low | ≤19.0 | ≤46.2 | 4 | No change |
| Intermediate | >19.0 and <57.4 | >46.2 and <154.8 | 6 | No change |
| High | ≥57.4 | ≥154.8 | 9 | Add moxifloxacin or clofazamine |

* ETS1/23S and ITS1/23S ratios are multiplied by $10^4$.

A second iteration is based on the reduction factor relative to pre-treatment baseline value. As defined in Methods above, the reduction factor indicates the fold-decrease from baseline (pre-treatment) pre-rRNA ratio. As above, for drug-susceptible TB, the reduction factor is typically calculated after 4 or 8 weeks of treatment. For MDR-TB or non-TB mycobacterial disease, the optimal sampling time could differ. As above, threshold reduction factors delineating low, intermediate and high risk for relapse groups were defined based quartiles in human clinical data.

TABLE 4

Illustration of the use of reduction factor thresholds to direct treatment duration or composition of antibiotic regimen for drug-susceptible TB. Reduction factors are calculated in sputum 4 or 8 weeks after treatment initiation.

|  |  |  | Action |  |
|---|---|---|---|---|
| Relapse risk | ETS1/23S reduction factor | ITS1/23S reduction factor | Treatment duration (months) | Antibiotic regimen |
| Week 4 |  |  |  |  |
| Low | ≥33.9 | ≥15.5 | 4 | No change |
| Intermediate | <33.9 and >14.0 | <15.5 and >3.5 | 6 | No change |
| High | ≤14.0 | ≤3.5 | 9 | Add moxifloxacin or clofazamine |
| Week 8 |  |  |  |  |
| Low | ≥57.4 | ≥24.1 | 4 | No change |
| Intermediate | <57.4 and >19.6 | <24.1 and >5.6 | 6 | No change |
| High | ≤19.6 | ≤5.6 | 9 | Add moxifloxacin or clofazamine |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of stratifying and treating a subject with a mycobacterial infection who is being administered a first therapeutic treatment against the mycobacterial infection, the method comprising:
   measuring at least one *Mycobacterium* pre-rRNA and at least one *Mycobacterium* mature rRNA in a biological sample that is obtained from the subject after the subject has received the first therapeutic treatment; and
   determining the ratio of the at least one *Mycobacterium* pre-rRNA and the at least one *Mycobacterium* mature rRNA in the biological sample;
   wherein:
      if the measured at least one *Mycobacterium* pre-rRNA/ *Mycobacterium* mature rRNA ratio is lower than about a first given value,
         the subject is stratified in a low risk group and further treated with the first therapeutic treatment for a first period of time; and
      if the measured at least one *Mycobacterium* pre-rRNA/ *Mycobacterium* mature rRNA ratio ranges from about the first given value to about a second given value, wherein the second value is higher than the first value,
         the subject is stratified in an intermediate risk group and further treated with the first therapeutic treatment for a second period of time,
      if the measured at least one *Mycobacterium* pre-rRNA/ *Mycobacterium* mature rRNA ratio is higher than about a second given value,
         the subject is stratified in a high risk group and further treated with both the first therapeutic treatment and a second therapeutic treatment for a third period of time;
      wherein the first period of time is shorter in magnitude than the second period of time, which is shorter in magnitude than the third period of time.

2. A method of determining if a subject with a *Mycobacterium* infection who is being administered a therapeutic treatment against the mycobacterial infection is responsive to the therapeutic treatment and treating the subject, the method comprising:
   measuring at least one *Mycobacterium* pre-rRNA and at least one *Mycobacterium* mature rRNA in a biological sample that is obtained from the subject after being administered the therapeutic treatment; and
   determining the ratio of the at least one *Mycobacterium* pre-rRNA and the at least one *Mycobacterium* mature rRNA in the biological sample;
   wherein, if the measured ratio is lower than about a given value, the subject is further administered the therapeutic treatment, and
   wherein, if the measured ratio is equal to or higher than about a given value, the subject is administered another therapeutic treatment comprising at least one selected from the group consisting of clofazimine, pyrazinamide, bedaquiline, levofloxacin, kanamycin, moxifloxacin, rifapentine, pretomanid, delamanid, linezolid, amikacin, capreomycin, rifabutin, and cycloserine.

3. A method of determining optimal duration of administration of a therapeutic treatment to a subject with a mycobacterial infection who is being administered a first therapeutic treatment against the mycobacterial infection, the method comprising at least one of the following:
   measuring at least one *Mycobacterium* pre-rRNA and at least one *Mycobacterium* mature rRNA in a biological sample from the subject that has been administered the first therapeutic treatment, wherein the Mycobacteria is drug-susceptible;
   determining the ratio of the at least one *Mycobacterium* pre-rRNA and the at least one *Mycobacterium* mature rRNA in the sample;
   wherein, if the ratio is lower than about a first value, then the subject is administered the therapeutic treatment for a first period of time,
   wherein, if the ratio ranges from about the first value to about a second value, wherein the second value is higher than the first value, then the subject is administered the therapeutic treatment for a second period of time, and
   wherein, if the ratio is higher than about the second value, the subject is administered both the therapeutic treatment and another therapeutic treatment for a third period of time;
   wherein the first period of time is shorter in magnitude than the second period of time, which is shorter in magnitude than the third period of time.

4. The method of claim 1, wherein the first therapeutic treatment comprises HRZE (isoniazid, rifampin, pyrazinamide and ethambutol).

5. The method of claim 1, wherein the *Mycobacterium* is multiple-drug-resistant.

6. The method of claim 1, wherein the pre-rRNA is at least one selected from the group consisting of ETS1, ITS1, and ITS2.

7. The method of claim 1, wherein the mature rRNA is at least one selected from the group consisting of 16S rRNA and 23S rRNA.

8. The method of claim 1, wherein the at least one *Mycobacterium* pre-rRNA/mature rRNA ratio is at least one selected from the group consisting of ETS1/16S rRNA, ETS1/23S rRNA, ITS1/16S rRNA, ITS1/23S rRNA, ITS2/ 16S rRNA, and ITS2/23S rRNA.

9. The method of claim 1, wherein the *Mycobacterium* is selected from the group consisting of *Mycobacterium tuberculosis* complex (MTBC) organism, and non-tuberculous *Mycobacterium* (NTM).

10. The method of claim 1, wherein the *Mycobacterium* is at least one selected from the group consisting of *M. abscessus, M. arupense, M. asiaticum, M. avium, M. chelonae, M. chimaera, M. cosmeticum, M. gordonae, M. intracellulare, M. kansasii, M. lentiflavum, M. mageritense, M. malmoense, M. neoaurum, M. kubicae, M. szulgai, M. tuberculosis,* and *M. xenopi*.

11. The method of claim 10, wherein at least the lung of the subject is infected with the *M. tuberculosis*.

12. The method of claim 1, wherein the first therapeutic treatment comprises at least one selected from the group consisting of isoniazid, rifampin, streptomycin, clofazimine, pyrazinamide, ethambutol, bedaquiline, levofloxacin, kanamycin, moxifloxacin, rifapentine, pretomanid, delamanid, linezolid, amikacin, capreomycin, rifabutin, and cycloserine.

13. The method of claim 1, wherein the second therapeutic treatment comprises at least one selected from the group consisting of clofazimine, pyrazinamide, bedaquiline, levofloxacin, kanamycin, moxifloxacin, rifapentine, pretomanid, delamanid, linezolid, amikacin, capreomycin, rifabutin, and cycloserine.

14. The method of claim 1, wherein the biological sample comprises at least one selected from the group consisting of sputum, saliva, bronchoalveolar lavage fluid, lung tissue and lymph node tissue.

15. The method of claim 1, wherein the measuring of the at least one *Mycobacterium* pre-rRNA and the at least one *Mycobacterium* mature rRNA comprises at least one method selected from the group consisting of RNAseq, qRT-PCR, Nanostring, and droplet digital PCR.

16. The method of claim 1, wherein the subject is a mammal.

17. The method of claim 16, wherein the mammal is human.

* * * * *

UNITED STATES PATENT AND TRADEMARK OFFICE
CERTIFICATE OF CORRECTION

PATENT NO. : 11,572,588 B2
APPLICATION NO. : 16/632310
DATED : February 7, 2023
INVENTOR(S) : Nicholas D. Walter et al.

It is certified that error appears in the above-identified patent and that said Letters Patent is hereby corrected as shown below:

In the Specification

In Column 1, after the heading "STATEMENT REGARDING FEDERALLY SPONSORED RESEARCH OR DEVELOPMENT," please replace the paragraph at Lines 22-25 with the following paragraph:
-- This invention was made with government support under 200-2009-32597 awarded by the Centers for Disease Control and Prevention, and AI068636, AI135652, and R01 AI127300 awarded by the National Institutes of Health. The government has certain rights in the invention. --

Signed and Sealed this
Second Day of January, 2024

Katherine Kelly Vidal
*Director of the United States Patent and Trademark Office*